United States Patent [19]

Dooka et al.

[11] Plant 4,502

[45] Feb. 12, 1980

[54] CARNATION NAMED DOOKA PINK

[76] Inventors: Akira Dooka; Michiko Dooka, both of 1621 Old San Jose Rd., Soquel, Calif. 95073

[21] Appl. No.: 937,088

[22] Filed: Aug. 28, 1978

[51] Int. Cl.[2] ..... A01H 5/00

[52] U.S. Cl. ..... Plt./70

[58] Field of Search ..... Plt./70-71

*Primary Examiner*—Robert E. Bagwill

*Attorney, Agent, or Firm*—Charles W. Rummler

[57] ABSTRACT

A new variety of spray type or miniature carnation plant distinguished by its profuse production of well formed variegated pink and white flowers borne on strong stems of relatively short length; by its vigorous and upright growth habit and abundant foliage; and by its continuous flowering habit with small, fragrant and long lasting blooms.

1 Drawing Figure

BACKGROUND OF THE NEW PLANT

This carnation cultivar originated as a sport of Ocean Spray (P.P. 3299) and was discovered by us at our nursery in Soquel, Calif. The lovely pink coloring of the flower led us to propagate this sport at our nursery by cuttings and observation of the resulting plants, their growth and blooming habits, and the longevity and fragrance of the blooms has caused us to begin production of this plant for the commercial market. Propagation of this plant is now being done by cuttings at Salinas, Calif., as well as at Soquel, Calif., and many generations of this plant have demonstrated that its distinctive characteristics hold true and appear to be firmly fixed.

DESCRIPTION OF THE DRAWING

Our new variety of carnation plant is illustrated by the accompanying full color photographic drawing which shows a spray of fully opened flowers and several stages of buds, the color rendition being as nearly true as it is reasonably possible to obtain by conventional and professional photographic procedures.

DESCRIPTION OF THE NEW PLANT

The following is a detailed description of our new carnation cultivar based upon observations made of plants grown under conventional greenhouse practices at Salinas, Calif., the color descriptions being according to the R.H.S. Colour Chart published by The Royal Horticultural Society of London, England, in collaboration with the British Colour Council.

THE PLANT

Origin: Sport
Parentage: Ocean Spray (P.P. 3299)
Classification:
*Botanic.*—Dianthus.
*Commercial.*—Miniature Carnation.
Form: Upright bush.
Height: Main stems or canes — about 57 cm.
Growth: Vigorous, strong and upright.
Branching habit: Moderate side shoots.
Foliage: Abundant, usually 24 leaves per spray.
*Leaf size.*—About 8 cm. long.
*Shape.*—Lanceolate and pointed.
*Margin.*—Entire.
*Texture.*—Smooth.

*Color.*—Upper side — Greyed Green 191A. Under side — Greyed Green 191A.

THE BUD

Form: Generally ovoid and pointed.
Size: About 3 cm. long and 1.5 cm. in diameter.
Opening rate: Moderate.
Calyx: Size — 3.5 cm. long; 1.4 cm. wide.
*Shape.*—Elongated with long point.
*Splitting.*—None.
*Aspect.*—Smooth.
Sepals: Shape — generally oval with mucronate tip.
*Condition.*—Hooded over bud; upstanding when flowers open.
*Color.*—Inside and outside — 191A.
Peduncle: Erect and rigid.
*Color.*—191A.

THE FLOWER

Blooming habit: Continuous and profusely.
Size of bloom: Small.
*Diameter.*—About 5 cm.
*Depth.*—About 4 cm.
Shape: High center when first opening and at maturity.
Petalage: Number of petals — 32.
*Arrangement.*—Generally imbricated.
*Form.*—Fan shaped with frilled end margins.
*Texture.*—Soft.
*Aspect.*—Satiny.
Color:
Outer petals.—Upper side — mainly Red Purple 66C with white base and streaks or splotches of white in the petal body. Under side — mainly 65D with white base portion.
*Inner petals.*—Upper side — mainly 66D with white base and streaks of white in many petals, some petals having the white streaks extending from end-to-end. Under side — 65D with white base portion.
Peduncle: Flowering stem — rigid and upright.
*Color.*—Greyed Green 191A.
Discoloration after full bloom: Very slight.
Persistence: Petals hang on and dry.
Fragrance: Spicy carnation.
Disease resistance: Resistant to botrytis where that disease often occurs.
Lasting quality: 5 weeks on plant; 3 weeks as cut flower.

REPRODUCTIVE ORGANS

Stamens: Number — 4.
*Anthers.*—2.4 mm. in size.
*Filaments.*—1.5 cm. long. Color — white.
*Pollen.*—None.
Pistils: Number — 2.
*Styles.*—1.2 cm. long. Color — white.
*Stigmas.*—Color — white.
Ovaries: Ovoid in shape and segmented.

This new variety of spray type carnation most nearly resembles its parent Ocean Spray differing particularly by the pink coloration of its flowers.

I claim:

1. A new and distinct carnation cultivar substantially as herein shown and described, characterized by its profuse and continuous production of relatively small variegated pink and white flowers on strong, rigid stems.

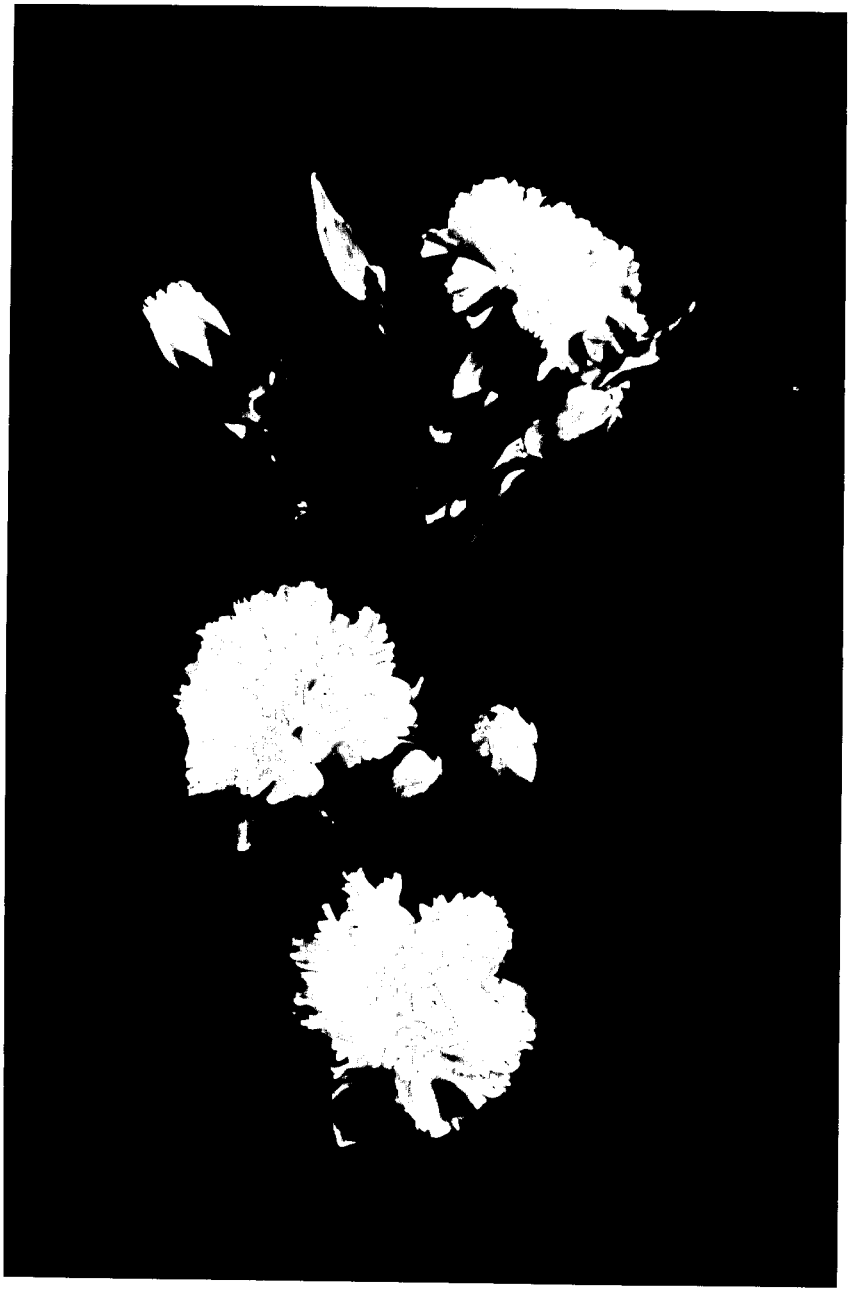

* * * * *